United States Patent [19]
Parsi

[11] Patent Number: 4,731,049
[45] Date of Patent: Mar. 15, 1988

[54] CELL FOR ELECTRICALLY CONTROLLED TRANSDERMAL DRUG DELIVERY

[75] Inventor: Edgardo J. Parsi, Lexington, Mass.

[73] Assignee: Ionics, Incorporated, Watertown, Mass.

[21] Appl. No.: 9,301

[22] Filed: Jan. 30, 1987

[51] Int. Cl.[4] .............................................. A61N 1/30
[52] U.S. Cl. ..................................... 604/20; 128/803
[58] Field of Search ...................... 604/20, 42; 128/803

[56] References Cited

U.S. PATENT DOCUMENTS

| | | | |
|---|---|---|---|
| 4,141,359 | 2/1979 | Jacobsen et al. | 604/20 |
| 4,181,128 | 1/1980 | Swartz | 604/20 |
| 4,250,878 | 2/1981 | Jacobsen et al. | 604/20 |
| 4,406,658 | 9/1983 | Lattin et al. | 604/20 |
| 4,416,274 | 11/1983 | Jacobsen et al. | 604/20 |
| 4,419,092 | 12/1983 | Jacobsen et al. | 604/20 |
| 4,474,570 | 10/1984 | Arivra et al. | 604/20 |
| 4,602,909 | 7/1986 | Csillik et al. | 604/20 |
| 4,640,689 | 2/1987 | Sibalis | 604/20 |

Primary Examiner—Edward M. Coven
Attorney, Agent, or Firm—Norman E. Saliba

[57] ABSTRACT

A cell for electrically controlled drug delivery into and through the skin consisting of a source of current, an electrode, and a drug reservoir in which a drug is bound by an ion exchange medium or an immobilized ligand affinity medium. An additional ion reservoir may be interposed between the electrode and the drug reservoir and semi-permeable membranes are employed as barriers between the various components of the device as required.

9 Claims, 2 Drawing Figures

CELL FOR ELECTRICALLY CONTROLLED TRANSDERMAL DRUG DELIVERY

BACKGROUND OF THE INVENTION

1. Field of the Invention:

The invention resides in the field of devices for the controlled delivery of drugs and more particularly relates to cells for the transdermal application of drugs using electrical current.

2. Description of the Prior Art:

Controlled delivery through the skin by the use of electrical current is known in the prior art. Devices heretofore employed for such purposes include a source of current, a drug reservoir, an application electrofde communicating with the reservoir and a semi-permeable membrane positioned between the reservoir and the skin. The circuit is completed by an additional grounding electrode attached to the skin resulting in the transfer of a drug in ionic form from the reservoir, through the membrane and into and through the skin. The method is particularly advantageous for applying therapeutic substances directly to a situs of concern without intrusion into the body as a whole. Thus by use of these basic devices disclosed in, for example, U.S. Pat. Nos. 4,166,457 and 4,250,878, Jacobsen et al, showing various forms of suitable electrodes, this method allows a concentrated, regulated delivery of a selected drug.

The approach is of recognized benefit for specific medical applications and refinements in the above described apparatus such as a current control device detailed in U.S. Pat. No. 4,141,359 to the same inventor are emerging as a matter of course.

However, as known to the present inventor, this technique, designated generally as epidermal iontophoresis, is presently limited to drugs which are in the free ionic state in the reservoir. Many additional drugs are known which can be bound to an ion exchange medium or to an immobilized ligand affinity medium. These compounds may be desorbed from their carrier media directly by cations or anions generated at an electrode in communication with the drug reservoir or by ions contained in an intermediate ion reservoir between the electrode and the drug reservoir and transferred by the application of an electrical current. In contrast, therefore to those devices and their method of use known in the prior art, the present invention facilitates the employment of a much wider field of therapeutic materials than has been previously possible.

SUMMARY OF THE INVENTION

The present invention may be summarized as a cell for electrically controlled transdermal drug delivery by iontophoresis, i.e., the transfer of a subject substance by ion migration through the application of electric current. In the invention, the desired drug is bound on an ion exchange resin or medium or an immobilized ligand affinity medium located in the drug reservoir. The delivery occurs upon the application of an electrical current of generally small proportions to the reservoir or to an adjacent ion reservoir separated from the drug reservoir by a semi-permeable membrane. The drug reservoir is preferably separated from the skin by a hydrophilic medium (hydrogel) to swell the skin and facilitate the drug transfer.

While the most basic form of the invention employs a connection to the skin (or the hydrophilic medium next to the skin) of the opposite pole of the current source from that of the application electrode, it may be desirable to complete the circuit through a second buffering cell or electrode to neutralize the by-products of the ion transfer section. This second grounding electrode may be in contact with the primary drug containing cell separated by an insulating barrier or spaced apart therefrom on another portion of the skin.

These and other features and advantages of the invention will be more fully appreciated from the description of the preferred embodiment and drawing which follows.

DESCRIPTION OF THE PREFERRED EMBODIMENT

Figure 1:
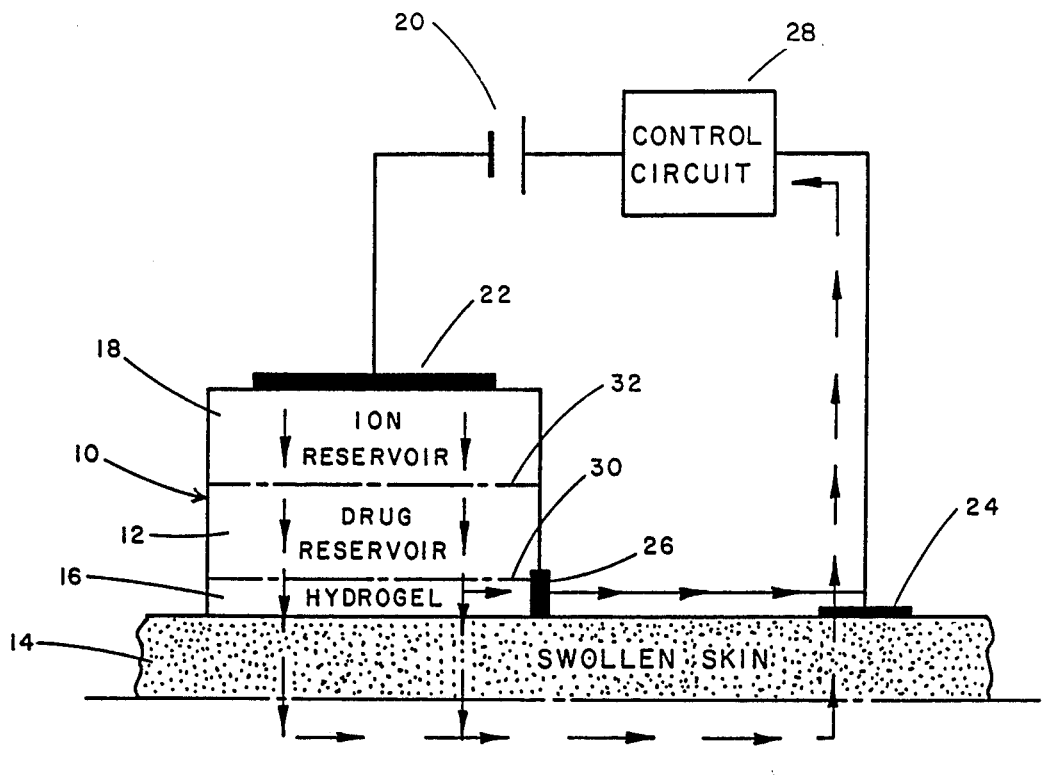
FIG. 1 is a schematic representation of the preferred embodiment of the invention.

FIG. 1 illustrates in schematic form the electrical cell which constitutes the preferred embodiment of the invention. Cell 10 is composed of an impervious biocompatible material such as a polyurethane or other polymer and may be flexible or not as the use requires. A reservoir 12 contains the species of interest such as a drug bound to an ion exchange medium or an immobilized ligand affinity medium. Beneath the reservoir 12 and in contact with the skin 14 there may be located a quantity of hydrophilic material 16 which functions to swell the skin to facilitate the drug transfer. This hydrophilic reservoir may contain hydrogels such as poly (hydrooxyethyl methacrylate) which is sold as Hydron® by hydron Laboratories, N.J., poly (vinyl-2-pyrrolidone), poly (vinyl alcohol) and water-soluble cellulose derivatives or other natural or synthetic materials which hold large amounts of water within their structure.

On the opposite side of drug reservoir 12, an ion reservoir 18 is positioned to provide a supply of cations or anions to effect the release of the drug upon application of an electric current from source 20 to adjacent electrode 22. It should be understood that the ion reservoir is not necessary for all transfer reactions, that is, in some cases, particularly where the drug is bound to an immobilized ligand affinity medium, sufficient ions for release may be formed directly at the electrode 22 which is in direct contact with the drug reservoir itself.

The circuit is completed from the opposite pole of the current source 20 to an adjacent area of the skin 24 or alternatively to the hydrophilic medium at electrically conducting area 26. In the former case the current (as shown by the arrows) flows through the skin and drives the drug into and through the skin. In the latter case the current desorbs the drug into the hydrophilic reservoir 16, where it is free to diffuse through the skin. It is of course understood that one would employ either circuit arrangement (i.e. the former or latter case) alone as so desired and not together in a simultaneous process.

A control device 28 for activating the cell 10 may take the form of an on-off switch, a timer, and an electrical resistor, fixed or variable. Other more sophisticated electronic control devices are well know, such as microchips, which could be preprogrammed to control the dosage, or in the optimal limiting case respond to sensor signals to regulate the dosage to maintain a certain preset or preprogrammed level.

Suitable semi-permeable membranes 30 and 32 well known in the art are employed as barriers to separate the various components of the cell as required and may be either cation or anion selective depending upon the nature of the drug and its binding medium and the polarity of the electrodes. Alternatively, membrane 30 can be a porous non ion-selective barrier such as an ultrafiltration or microfiltration membrane which are well known in the art. Although the cell can operate without positioning a semi-permeable barrier 30 between the drug reservoir 12 and the hydrophilic reservoir 16, it is preferred that such barrier be present.

It is intended that the invention be used for drugs that will be released by either cations or anions as the combination of drug and binding media requires. Thus the ion reservoir where required may be either a cation reservoir or an anion reservoir. Examples of suitable cations released from appropriate compounds in solution are hydrogen, sodium, and potassium ions and suitable anions are hydroxyl, chloride, and sulfate ions.

In the case of basic nitrogen-containing drugs, for example, a sulfonic acid cation exchange resin or media may be utilized to bind the drug, and under the applied electrical potential the drug is displaced from the drug-resin complex by the cations held in the cation reservoir 18 adjacent to drug reservoir 12. A cation selective membrane 32 may be used to separate the cation reservoir and the drug reservoir. Examples of drugs which may be absorbed onto a sulfonic acid cation exchange media are codeine, chlorpheniramine, phenylpropanolamine (amphetamine) and the like.

The ion exchange media can be in the form of beads, powder, packed fibers, woven or knit fibers, microporous or macroreticular resin, or liquid resins.

In the embodiment of the invention utilizing an immobilized ligand affinity medium to bind the drug, that affinity medium can consist of materials which can be chemically activated by the cyanogen bromide or carbonyl diimidazole method for example, in order to covalently attach ligands such as, for example, Protein A (affinity for immunoglobin); monoclonal antibodies (with specific affinity for certain drugs) and certain dyes such as Cibacron Blue F3G-A dye (which has a broad range of specificity for proteins). Examples of such materials used as affinity chromatography matrices are agarose, cellulose, crosslinked dextran (Sephadex ®), cross-linked acrylamide and other media. Some of these materials are commercially available in their activated form, such as Reacti-Gel ® from Pierce Chemical Co., Rockford, Ill. and Immobilon ® from Millipore Corporation, Bedford, MA.

Figure 2:
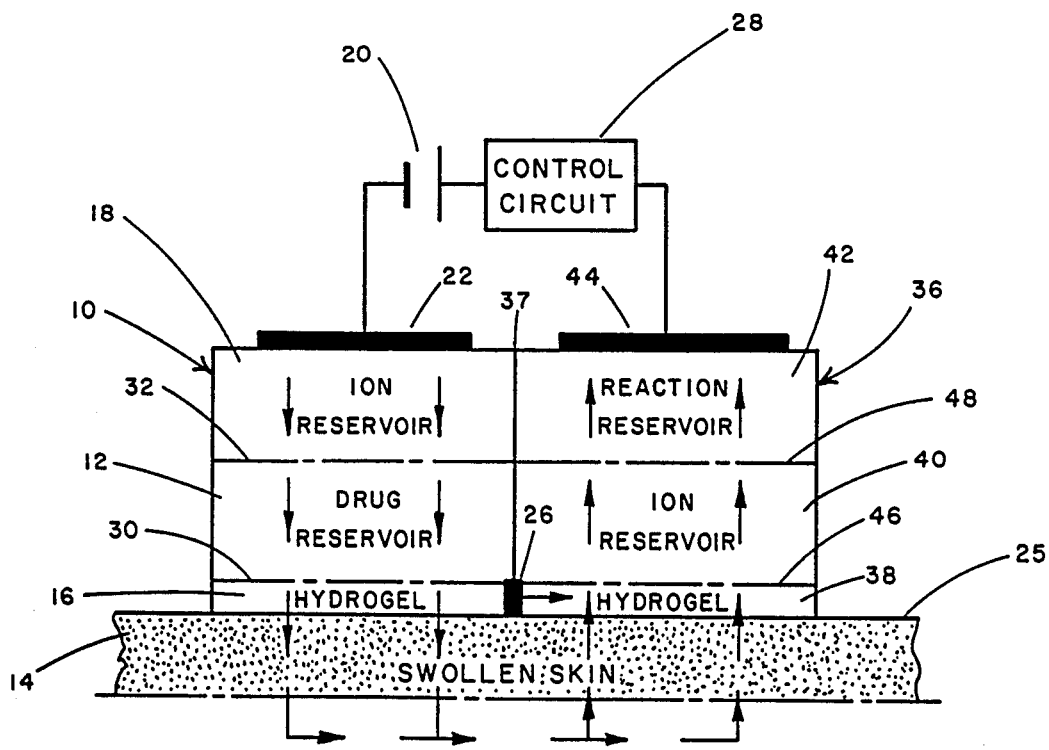
FIG. 2 is a schematic representation of an additional component of the preferred embodiment of FIG. 1.

Referring next to FIG. 2, the preferred embodiment is illustrated in conjunction with an additional cell which functions as an auxiliary electrode. Such may be desirable to neutralize any by-products of the transfer reactions discussed above, and avoid skin irritation or burning from by products of reactions occuring at electrode 44.

The grounding cell 36 which may be positioned adjacent to cell 10 and separated by an insulating barrier 37 (or spaced at another convenient location), consists of a hydrophilic medium reservoir 38 and an ion reservoir 40. Reservoir 40 contains appropriate buffering compounds to neutralize, for example, hydroxyl ions generated at the cathode when the polarity of the application cell is selected such that the drug in the drug reservoir is desorbed by cations or by hydrogen ions.

An additional reservoir 42 may be utilized to isolate ion reservoir 40 from direct contact with the neutralization reaction and the grounding electrode 44. As before, semi-permeable membranes 46 and 48 which may be ion selective form barriers between the several compartments of the grounding cell 36.

Alternatively, a high molecular weight compound capable of reacting with the unwanted by-products, hydroxyl ions for example, may be included in the hydrophylic medium reservoir 38 or the reaction reservoir 42.

Again as in the case of FIG. 1, the circuit need not be completed through the skin but instead may be completed through the hydrophilic media at 26. In this case, area 25 of the grounding cell 36 would be electrically insulating and the current is applied to release the drug into the hydrophilic reservoir 16 of the application cell 10 where the drug is free to diffuse into the adjacent skin layer.

The analogous case where the anode (instead of the cathode) is used to complete the electrical circuit will be apparent to those versed in the art.

The active surface of the electrodes employed may comprise carbon, graphite or metal, preferably the dimensionally stable type such as platinum group metals or oxides as such or in the form of a microcoat on valve metals such as titanium or niobium. The electrode may be in the form of wire, mesh or sheet according to the geometric design of the device.

A number of geometric designs can be employed to reduce the distance which the electric current must travel through the skin or between the drug-containing hydrogel and the neutral hydrogel, including, for example, annular, striped or intercalated and mosaic designs.

Although the invention has been described with reference to various specific and preferred embodiments and techniques, it should be understood that many variations and modifications may be made while remaining within the spirit and scope of the invention.

What is claimed is:

1. A cell for the electrically controlled delivery of a drug into and through the skin of a subject patient comprising in combination:
    a. a drug reservoir containing therein a drug bound to an immobilized ligand affinity medium or an ion-exchange medium;
    b. an electrode communicating with said reservoir; and
    c. a source of current connected between said electrode and said skin.

2. The apparatus of claim 1 further including a semi-permeable membrane interposed between said drug reservoir and the skin.

3. The apparatus of claim 2 further including a layer of hydrophilic medium interposed between said membrane and said skin.

4. A cell for use in the electrically controlled delivery of a drug into the skin of a subject patient comprising in combination:
    a. a drug reservoir containing therein a drug bound to an immobilized ligand affinity medium or an ion-exchange medium;
    b. a first semi-permeable barrier interposed between said drug reservoir and said skin;
    c. an ion reservoir positioned adjacent to said drug reservoir;
    d. a second semi-permeable barrier interposed between said drug reservoir and said ion reservoir;

e. an electrode communicating with said ion reservoir; and f. a source of current connected between said electrode and said skin.

5. The apparatus of claim 4 wherein said electrode comprises an anode and said ion reservoir comprises a cation reservoir.

6. The apparatus of claim 4 further including a hydrophilic reservoir interposed between said first semipermeable barrier and said skin.

7. The apparatus of claim 4 wherein said drug reservoir contains a drug bound on an ion exchange resin.

8. The apparatus of claim 4 wherein said drug reservoir contains a drug bound on an immobilized ligand affinity medium.

9. The apparatus of claim 4 further including an additional cell for grounding said cell containing said drug reservoir comprising in combination:

a. a second ion reservoir;

b. a second hydrophilic medium interposed between said skin and said second ion reservoir;

c. a semi-permeable barrier interposed between said second ion reservoir and said second hydrophilic medium; and d. a second electrode of opposite polarity to said drug reservoir electrode connected to said current source and communicating with said second ion reservoir.

* * * * *